(12) United States Patent
Hamilton et al.

(10) Patent No.: US 8,982,338 B2
(45) Date of Patent: Mar. 17, 2015

(54) SAMPLE ANALYSIS

(75) Inventors: Mark A. Hamilton, Upton, MA (US); Stanislaw Piorek, Hillsborough, NJ (US); Richard A. Crocombe, Winchester, MA (US)

(73) Assignee: Thermo Scientific Portable Analytical Instruments Inc., Tewksbury, MA (US)

( * ) Notice: Subject to any disclaimer, the term of this patent is extended or adjusted under 35 U.S.C. 154(b) by 408 days.

(21) Appl. No.: 13/485,194

(22) Filed: May 31, 2012

(65) Prior Publication Data

US 2013/0321793 A1 Dec. 5, 2013

(51) Int. Cl.
*G01N 21/00* (2006.01)
*G01N 21/65* (2006.01)

(52) U.S. Cl.
CPC ............ *G01N 21/65* (2013.01); *G01N 2223/00* (2013.01)
USPC .......................................................... 356/72

(58) Field of Classification Search
CPC .............................. G01N 21/65; G01N 23/223
USPC .......................................................... 356/301
See application file for complete search history.

(56) References Cited

U.S. PATENT DOCUMENTS

| | | | |
|---|---|---|---|
| 4,147,935 A * | 4/1979 | Warrikhoff | 378/98.6 |
| 5,206,699 A | 4/1993 | Stewart et al. | |
| 6,081,577 A * | 6/2000 | Webber | 378/23 |
| 6,801,595 B2 | 10/2004 | Grodzins et al. | |
| 7,269,245 B2 * | 9/2007 | He et al. | 378/71 |
| 7,636,157 B2 | 12/2009 | Wang et al. | |
| 7,701,571 B2 | 4/2010 | Azimi et al. | |
| 7,791,027 B2 | 9/2010 | McAllister et al. | |
| 7,875,847 B2 | 1/2011 | Dugas et al. | |
| 7,916,834 B2 | 3/2011 | Piorek et al. | |
| 7,928,391 B2 | 4/2011 | Azimi et al. | |
| 7,945,393 B2 * | 5/2011 | Treado et al. | 702/19 |
| 8,081,305 B2 | 12/2011 | Azimi et al. | |
| 8,107,069 B2 | 1/2012 | Wang et al. | |
| 2007/0085025 A1 * | 4/2007 | Eggeling et al. | 250/459.1 |
| 2007/0192035 A1 * | 8/2007 | Schweitzer et al. | 702/19 |
| 2008/0117408 A1 * | 5/2008 | Kim et al. | 356/51 |
| 2008/0158544 A1 * | 7/2008 | Womble et al. | 356/39 |

(Continued)

FOREIGN PATENT DOCUMENTS

WO 8801378 A1 2/1988

OTHER PUBLICATIONS

Florian Knorr, "Development of a time-gated system for Raman spectroscopy of biological samples", Sep. 13, 2010.*

(Continued)

*Primary Examiner* — Kara E Geisel
*Assistant Examiner* — Maurice Smith
(74) *Attorney, Agent, or Firm* — Ion C. Abraham (57) ABSTRACT

An analyzer for analyzing a composition of a sample, and methods of operating an analyzer. The analyzer may include an optical illuminator and a Raman spectrometer to produce Raman spectral data representative of Raman radiation emitted from the sample in response to the illuminating light. Features to reduce background fluorescence are optionally provided. An x-ray illuminator may be provided to illuminate the sample with x-rays, and also an x-ray spectrometer may be present to produce x-ray spectral data representative of fluorescence radiation emitted from the sample in response to the illuminating x-rays. A processor receives the Raman spectral data and any x-ray spectral data and provides an analysis of a compound in the sample.

24 Claims, 7 Drawing Sheets

(56) References Cited

U.S. PATENT DOCUMENTS

| | | | |
|---|---|---|---|
| 2009/0012723 A1* | 1/2009 | Treado et al. | 702/28 |
| 2009/0057422 A1 | 3/2009 | Dugas et al. | |
| 2009/0190722 A1* | 7/2009 | Windt | 378/206 |
| 2009/0213361 A1 | 8/2009 | Vander Rhodes et al. | |
| 2010/0165335 A1* | 7/2010 | Tearney | 356/301 |
| 2010/0191493 A1 | 7/2010 | Brown et al. | |
| 2010/0315629 A1 | 12/2010 | Knopp et al. | |
| 2011/0079734 A1 | 4/2011 | Grodzins et al. | |

OTHER PUBLICATIONS

Andrikopoulos "In vitro validation of a mobile Raman-XRF micro-analytical instrument's capabilities on the diagnosis of Byzantine icons", Dec. 18, 2005.*

Rui Liu, "Applications of Raman-based techniques to on-site and in-vivo analysis", Jul. 21, 2011.*

Andrikopoulos et al., In vitro validation of a mobile Raman-XRF micro-analytical instrument's capabilities on the diagnosis of Byzantine icons, J of Raman Spectroscopy, 37, 1026-1034, 2006.

Asher and Johnson, Raman spectroscopy of a coal liquid shows that fluorescence interference is minimized with ultraviolet excitation, Science, 225, 311-313, 1984.

Asher, UV resonance Raman spectroscopy for analytical, physical and biophysical chemistry, Part 1, Analytical Chemistry, 65(2), 59-66, 1993.

Asher, UV resonance Raman spectroscopy for analytical, physical and biophysical chemistry, Part 2, Analytical Chemistry, 65(4), 201-210, 1993.

Asher, Handbook of vibrational spectroscopy, Chalmers and Griffiths, Eds., John Wiley & Sons Ltd., 1-15, 2002.

Blacksberg et al., Time-resolved Raman spectroscopy for in situ planetary mineralogy, Applied Optics, 49(26), 4951-4962, 2010.

Brostoff et al., Combined X-ray diffraction and Raman identification of synthetic organic pigments in works of art: from powder samples to artists' paints, Analytical Chemistry, 81(15), 6096-6106, 2009.

Burgio et al., Raman microscopy and X-ray fluorescence analysis of pigments on medieval and Renaissance Italian manuscript cuttings, PNAS, 107(13), 5726-5731 (2010).

Das and Hendry, Application of Raman spectroscopy to identify iron minerals commonly found in mine wastes, Chemical Geology, 290, 101-108 (2011).

Jehlicka et al., Application of portable Raman instruments for fast and non-destructive detection of minerals on outcrops, Spectrochimica Acta Part A, 73, 410-419 (2009).

Sparrow et al., New 224 nm hollow cathode laser-UV Raman spectrometer, Applied Spectroscopy, 55(1), 66-70, 2001.

Van Sprang et al., Fundamental parameter methods in XRF spectroscopy, JCPDS-International Centre for diffraction data 2000, Advances in X-ray analysis, 42, 1-10, 2000.

White, Last Raman spectroscopy as a technique for identification of seafloor hydrothermal and cold seep minerals, Chemical Geology, 1-13, article in press, 2008.

Janssens et al., Praxis: a combined micro-Raman—micro-XRF instrument, IXCOM 2005, 45 pages.

* cited by examiner

SAMPLE ANALYSIS

FIELD

This invention generally relates to analyzing a sample, for example a mineral sample.

BACKGROUND

In many applications it is desirable to obtain an analysis of a sample of interest. The analysis desired may be qualitative, quantitative, or both, and may be of only one or of multiple elements or compounds in a sample. For example, in mining applications, such as oil and gas exploration, it is desirable to analyze multiple samples for the presence of one or more minerals. This type of analysis can directly provide analytical information on a mineral which is sought or can provide analytical information on an indicator mineral which may suggest nearby locations of a mineral or other deposit which is sought. For example, by understanding the mineral makeup of a sample, one can identify the possibility that an area being explored is more or less likely to contain oil, gas or oil/gas bearing formations.

X-ray fluorescence ("XRF") is a technique which has been used for elemental analysis of various samples, including minerals. An XRF analyzer determines the chemistry of a sample by illuminating a spot on the sample with x-rays and measuring the spectrum of characteristic x-rays emitted by the different elements in the sample. The primary source of x-rays may be an x-ray tube or a radioactive material, such as a radioisotope. The term "x-rays" as used herein, includes photons of energy between about 1 keV and about 150 keV and will, therefore, include: the characteristic x-rays emitted by an excited atom when it deexcites; bremsstrahlung x-rays emitted when an electron is scattered by an atom; elastic and inelastically scattered photons generally referred to as Rayleigh and Compton scattered radiation, respectively.

When exposed to high energy primary x-rays from a source, each atomic element present in a sample produces a unique set of characteristic fluorescence x-rays that are essentially a fingerprint for the specific element. An x-ray fluorescence analyzer determines the chemistry of a sample by illuminating a spot on the sample with x-rays and measuring the spectrum of characteristic x-rays emitted by the various elements in the sample. The primary source of x-rays may be an x-ray tube or a radioactive material, such as a radioisotope. At the atomic level, a characteristic fluorescent x-ray is created when a photon of sufficient energy strikes an atom in the sample, dislodging an electron from one of the atom's inner orbital shells. The atom then nearly instantaneously regains stability, filling the vacancy left in the inner orbital shell with an electron from one of the atom's higher energy (outer) orbital shells. Excess energy may be released in the form of a fluorescent x-ray, of an energy characterizing the difference between two quantum states of the atom. By inducing and measuring a wide range of different characteristic fluorescent x-rays emitted by the different elements in the sample, XRF analyzers are able to determine the elements present in the sample, as well as to calculate their relative concentrations based on the number of fluorescent x-rays occurring at specific energies. However, except in special circumstances, low concentrations of light elements (those with low atomic number, Z, typically below 20) cannot typically be measured directly with portable XRF analyzers because fluorescent x-rays with energies below about 2.5 kiloelectron volts (keV) are absorbed within short path lengths of air. For this reason, light element XRF analysis requires either a helium gas purge or the evacuation of the volumes through which the relevant x-rays pass, which can be inconvenient for a portable or hand-held instrument.

XRF analyzers are well known, and include those described in U.S. Pat. Nos. 7,875,847, 7,916,834, and 7,791,027, which are incorporated herein by reference.

SUMMARY

The present invention realizes that the complete elemental analysis provided by XRF is often not feasible for analyzing samples. For example, in the above mentioned mining applications the identified minerals to be analyzed are often inorganic compounds containing one or more lighter elements such as magnesium, oxygen, sulfur, or the like. However, detection of elements lighter than magnesium by XRF is problematic as already described. Therefore, limited information is gained via XRF for many minerals because the majority of them consist of mixture of oxides of aluminum, and silicon. A similar situation occurs with plastics/polymers, composed principally of carbon and hydrogen, with some nitrogen and oxygen. The present invention also realizes that in such situations the inability of XRF to directly measure light elements such as oxygen, nitrogen and carbon negatively affects the accuracy of analysis for other elements/constituents of sample which can be analyzed by XRF.

Accordingly, the present invention provides in some embodiments an apparatus and a method for analyzing a composition of a sample wherein the sample is illuminated with x-rays to obtain x-ray spectral data, and also illuminated with light to obtain Raman spectral data. An analysis of the sample is provided based on both the x-ray spectral data and the Raman spectral data. In some embodiments a first element is identified based on the x-ray spectral data and a molecule is identified based on the Raman spectral data, with a compound being identified based on the identified element and molecule. In other embodiments, techniques are provided to reduce the effect of optical fluorescence which may be interfering with the Raman spectral data. For example, such techniques may use UV illuminating light such as UV light of less than 300 nm in wavelength, or may use anti-Stokes Raman spectral data to identify the molecule when the Stokes Raman spectral data is obscured by interfering optical fluorescence, or may select the Raman spectral data on the basis of time following a pulse of the light (for example, based on time following the beginning of the light pulse). In some embodiments, the apparatus and method may omit the x-ray illumination and x-ray spectrometer. In still other embodiments a quantitative analysis of a first element of a compound in the sample is provided based on the x-ray spectral data, and the presence of a second element is identified from the Raman spectral data.

Computer program products carrying a computer program which can execute a method of the present invention when loaded into a computer, are also provided.

DRAWINGS

Embodiments of the invention will now be described in which:

FIG. 2A is a top view of a hand-held analyzer of the present invention, while FIG. 2B is a side cross-section;

In the figures, the same reference numerals are used to represent the same or similar components.

DETAILED DESCRIPTION OF EMBODIMENTS

As mentioned above, embodiments of the present invention make use of a Raman spectral data obtained from a sample in response to illuminating the sample with light. Raman spectroscopy is an effective tool for identifying and characterizing a vast array of molecules. In Raman spectroscopy, a sample is illuminated with light typically from a laser and of a known wavelength (typically visible, or near infrared, but also ultraviolet). The laser light (also sometimes referred to as the Raman pump) interacts with the electron clouds in the molecules of the specimen and, as a result of this interaction, experiences selected wavelength shifting representing differences between the vibrational and/or rotational energy levels of the molecule. The precise nature of this wavelength shifting depends upon the molecules present in the specimen and can include both a Stokes shift (where the emitted photon is of longer wavelength than the incident or illuminating photon) and an anti-Stokes shift (where the emitted photon is of shorter wavelength that the incident photon). However, because they arise from molecules in excited vibration states, anti-Stokes spectra are lower in intensity than Stokes spectra, and also diminish in intensity with greater anti-Stokes shifts. A unique wavelength signature (typically called the Raman signature, or Raman spectrum) is produced by each molecule. This unique Raman signature permits the molecule to be identified and characterized. More specifically, the spectrum of light returning from the specimen is analyzed with an optical spectrometer so as to identify the Raman-induced wavelength shifting in the Raman pump light, and then this resulting Raman spectrum is compared (for example, by a processor) with a library of known Raman signatures so as to identify a molecule in the sample. Raman theory, including the Stokes/anti-Stokes ratio is described, for example, in D. A. Long, "Raman Spectroscopy", McGraw-Hill, 1977, particularly at pages 82-84.

Raman spectroscopy is widely used in scientific, commercial and public safety areas. Recent technological advances have made it possible to significantly reduce the size and cost of Raman spectroscopy systems. This has in turn increased the range of practical applications for Raman spectroscopy. For example, portable units have recently become available for various field uses, such as the on-site identification of potentially hazardous substances. Details of analyzers using Raman spectroscopy and spectra interpretation can be found, for example, in U.S. Pat. Nos. 8,107,069, 8,081,305, 7,928,391, 7,701,571, 7,636,157, 8,107,069, and U.S. patent publications US2009/0213361, US2010/0191493, US2010/0315629 (all of which references are incorporated herein by reference), and elsewhere. The design of Raman spectrometers, including discussions of lasers and detectors, is also described in Richard L. McCreery, "Raman Spectroscopy for Chemical Analysis", Wiley-Interscience, 2000. Raman spectra of some minerals have been reported, for example in "Handbook of Infrared and Raman Spectra of Inorganic Compounds and Organic Salts, Four-Volume Set", Richard A. Nyquist, Curtis L. Putzig and M. Anne Leugers, Academic Press, San Diego, 1997. However, the present inventors recognize that in practice Raman spectroscopy can encounter difficulty in analyzing many minerals. In particular, it has been found that many minerals contain materials which are strongly optically fluorescent in response to the typical illuminating wavelengths used in Raman spectroscopy, for example in "Luminescence Spectroscopy of Minerals and Materials", Michael Gaft, Renata Reisfeld and Gerard Panczer, Springer-Verlag, Berlin Heidelberg, 2005. Optical fluorescence (which term is used to include optical luminescence) arises from trace quantities of transition element and rare earth ions. For instance, Mn2+ and other divalent cations can substitute for Ca2+, while Fe3+ and Cr3+ can substitute for Al3+. Fluorescence and luminescence are much more efficient processes than Raman scattering with the quantum yield for fluorescence approaching unity, whereas approximately only 1 in $10^6$ photons are Raman scattered. Therefore very low levels of fluorescent impurities (parts per billion, parts per million) can produce optical signals equal to or much greater than Raman scattering and often obscure Raman spectra. This appears to result from the noise in the fluorescence signal being larger than the Raman signal, such that the Raman signal cannot be observed. In particular, a study by the present inventors of approximately 100 minerals and certified reference materials, has found that useful Raman spectra could only be obtained from only ~20% of these, despite using different exciting wavelengths of 785 nm, 532 nm and 1064 nm.

Embodiments of the present invention then, provide an analyzer for analyzing a composition of a sample, which analyzer includes an x-ray illuminator to illuminate the sample with x-rays and an x-ray spectrometer to produce x-ray spectral data representative of fluorescence radiation emitted from the sample in response to the illuminating x-rays. The analyzer also includes an optical illuminator to illuminate the sample with light, and a Raman spectrometer to produce Raman spectral data representative of the Raman radiation emitted from the sample in response to the illuminating light. A processor receives the x-ray fluorescence spectral data and the Raman spectral data and provides an analysis of a compound in the sample based on both signals.

In some embodiments the processor controls the x-ray and optical illuminators so as to turn them on sequentially. This sequential turning on may be done such that either one is turned on immediately after the other is turned off, or gaps in time may be provided when either one is turned off and before the other is turned on. Of course, the x-ray and optical illuminators may make simultaneous measurements.

In other embodiments the analyzer may optionally omit the x-ray illuminator and x-ray spectrometer, in which case the processor may provide an analysis of a molecule (which may be a compound) based only on the Raman spectral data. Again, in any embodiment an "analysis" may simply be an identification of a molecule (that is, a qualitative analysis that a molecule is present), though quantitative information may also be provided.

In any embodiment the processor may identify a first element of the compound based on the x-ray spectral data (when an x-ray illuminator and x-ray spectrometer are present), and also identify a molecule of the compound based on the Raman spectral data. The processor may then identify the compound based on any identified element and the identified molecule. For example, if the first element has been identified as strontium and the molecule identified as sulfate, then depending on anything else that may be identified as present, the compound might be identified as strontium sulfate. Optionally, the processor may identify the presence of a second element based on the Raman spectral data, typically simply from the identified molecule. For example, if a sulfate molecule was identified then the presence of sulfur and oxygen (in a ratio of 1 to 4) can be inferred. When one or more second elements are identified in this manner, the processor may provide a quantitative analysis of the first element based on the fluorescence signal and the presence of the second element. For example, information on the presence of a second element (such as concentration present or approximate concentration present) can be used in a fundamental parameters type calculation applied to x-ray spectra to more accurately analyze the concentration of a first element. The use of fundamental parameter calculations has been described, for example, in "FUNDAMENTAL PARAMETER METHODS IN XRF SPECTROSCOPY", Advances in X-ray Analysis, Vol. 42 by Hans A. van Sprang. Any of the foregoing methods may be performed for multiple elements or multiple molecule types and compounds.

Any of the embodiments of the present invention may include one or more methods of reducing or eliminating the effect of optical fluorescence which might otherwise interfere with the Raman spectral data. In a first one of such methods, an optical illuminator is used which illuminates the sample with UV light of less than 300 nm wavelength, or even less than 280 nm, less than 270 nm, or less than 260 nm (for example in the 200-250 nm range). Raman spectral data substantially free of interfering optical fluorescence can often be obtained in this manner. UV Raman spectrometry and its practice have been previously described by Sanford A. Asher "Ultraviolet Raman Spectrometry" appearing in The Handbook of Vibrations Spectroscopy", John Wiley & Sons, 2002. Of course, longer wavelength light (for example, visible or infra-red, such as up to 1500 nm or up to 1600 nm in wavelength) could be used in situations where fluorescence is not anticipated to be a problem for samples of interest, or where other methods of countering fluorescence is employed (such as those described following). In a second method wherein the Raman spectral data includes both Stokes anti-Stokes spectral data, the processor may determine if the Stokes spectral data is obscured by an interfering optical fluorescence signal. That is, whether an interfering optical fluorescence overlaps the Stokes spectra in location and intensity to a degree that the processor determines, for example based on preselected criteria, that the Stokes spectral data or some part of it is unreliable. Where the processor determines that the Stokes spectral data is obscured by an interfering optical fluorescence, it uses the anti-Stokes spectral data to identify the molecule and does not use the Stokes spectral data. Where the processor determines that the Stokes spectral data is not obscured by an interfering optical fluorescence, it uses the Stokes spectral data and not the anti-Stokes spectral data for the identification (since, as pointed out above, the Stokes spectra are typically of higher intensity). Of course, the processor may use both Stokes and anti-Stokes spectral data for the foregoing purpose, particularly where the Stokes signal is not obscured by an interfering optical fluorescence, or use part of one along with part, or all, of the other. In a third method the optical illuminator illuminates the sample with a light pulse (for example, under the control of the processor), and the processor selects the Raman spectral data from the Raman spectrometer on the basis of a preselected time following the light pulse. This is done so as to separate the Raman spectral data from an interfering optical fluorescence signal when present. Of course, this separation in time may not be perfect. Light pulse duration may be 1000 picoseconds or less, for example 500 picoseconds or less, 300 picoseconds or less, 200 picoseconds or less, or 100 picoseconds or less. The processor may select as the Raman spectral data, that data from the Raman spectrometer produced in response to radiation emitted from the sample within a preselected time following the beginning of the light pulse (for example, such as within 1 microsecond, 100 nanoseconds, or even with 50 nanoseconds). For example the preselected time following the beginning of the light pulse may be equal to the duration of the light pulse or may be less or longer. Since Raman radiation is typically produced almost instantaneously and fluorescence radiation occurs within nanoseconds to milliseconds after exciting illumination, this third method can substantially reduce or eliminate interference of the optical fluorescence with the Raman spectral data. This third method may be referenced as "time-gating". Methods and apparatus for implementing time-gating are described, for example, in "Time-resolved Raman spectroscopy for in situ planetary mineralogy" APPLIED OPTICS, Vol. 49, No. 26 (September 2010).

The present invention contemplates that multiple light pulses may be generated as a series of light pulses and multiple sets of Raman spectral data obtained in the foregoing manner following the beginning of each pulse. In this case the Raman spectral data may be summed to reduce signal/noise ratio. Sufficient time may be allowed between light pulses to allow most, or substantially all, interfering optical fluorescence to decay. For example, at least 100 milliseconds, at least 10 milliseconds, or at least 1 millisecond, or as little as 100 microseconds, 10 microseconds, or 1 microsecond might be provided between the end of one pulse and the start of the next in a pulse sequence.

Rather than using preselected times for the purposes of time-gating, the present invention alternatively provides an adaptive time-gating technique. This technique recognizes that different sample types may have widely different fluorescing components. In this adaptive time-gating the optical illuminator illuminates the sample with a light pulse. The processor identifies as a cut-off an elapsed time after the beginning of a light pulse at which optical fluorescence interferes with Raman spectral data, then selects as Raman spectral data that data from the Raman spectrometer produced in response to radiation emitted from the sample within the cut-off after the beginning a light pulse. "Interferes" or "interference" in this context references substantial interference, and an amount of interference can have been pre-selected by the instrument or software designer, or by the user, as being unacceptable (for example, where the signal/noise ratio for the Raman spectral data resulting from a single pulse would be decreased, or decreased by more than 10%, 20%, or 40%). The pulse (which as mentioned below, may be one or more pulses) following which the cut-off is identified in this manner can be the same or different from the pulse (again, including one or more pulses) following which the Raman spectral data is selected. Also, the samples may be different between these pulses, such that the cut-off is identified for one type of sample (for example, from a mineral sample collected from a location) and Raman spectral data is collected from multiple samples of the same type (for example, from mineral samples collected from the same location) using that identified cut-off. A different cut-off may be identified for different sample types (for example, different mineral samples from different locations, or sample types which are known or suspected to contain different types or amounts of fluorescing materials). Alternatively, the analyzer may be set to automatically determine a cut-off each time any new sample is placed in the analyzer for analysis.

In the described adaptive time-gating, the processor may also control the optical illuminator to produce a series of light pulses which are spaced (beginning to beginning) by at least the cut-off time (for example, the cut-off time, at least 10% or 50% more than the cut-off, or at least 2, 3 or 10 times the cut-off time or some greater multiple of the cut-off). Also, a variation the adaptive time-gating could be used in a same manner to alternatively or additionally adjust pulse intensity and length between samples or sample types so as to reduce the interference of fluorescence with Raman spectral data which might otherwise occur when samples or sample types are changed.

In one embodiment of the invention, an analyzer is provided according to any of the constructions herein, wherein the optical illuminator comprises a scanning optical illuminator. In a method of using such an analyzer, the scanning optical illuminator illuminates the sample with a beam of light scanned across an area on the sample. This allows one to obtain a spectra at different regions across the sample which may be useful in identifying different compositions at different regions of inhomogeneous samples. In another embodiment the optical illuminator could simply have a beam (such as a laser beam) which covers the same area as the X-ray illumination (for example, coextensive with the area of X-ray illumination). In this case, when a narrow beam, such as a laser beam, is used, then the beam can be expanded (such as by suitable optics) to have the same area as the x-ray illumination on the sample or scanned to cover the same area as the x-ray illumination of the sample. Of course, the areas can be matched in other manners, such as by suitable means or optics to shrink the x-ray beam so that it covers an area on the sample which is the same as that of the optical illumination.

Various constructions of any of the analyzer embodiments described herein are possible. In one embodiment the analyzer includes a housing having an optical port. For example, the x-ray illuminator, the optical illuminator, and the spectrometers may be positioned within the housing such that the x-ray illuminator and optical illuminator illuminate the sample out through the optical port and the spectrometers receive radiation from the sample passing back through the optical port. In this event, the x-ray illuminator may be positioned with a shorter path length to the optical port than the optical illuminator, and the x-ray spectrometer may be positioned with a shorter path length from the optical port than the Raman spectrometer. Since x-rays tend to become more attenuated over distance, particularly in the absence of a vacuum or special gases whereas light is not as sensitive to attenuation, the foregoing arrangements assists in keeping x-ray attenuation low while allowing components to be packed in a compact manner for hand-held or portable analysis devices. By "path length" in the foregoing context is meant the length of a path the X-rays or light take from the last optical component in their respective illuminators to the optical port, or the length of a path the x-ray fluorescence or Raman radiation take from the optical port to the first optical component in their respective spectrometers. In any embodiment, the x-rays and light may overlap (including being coextensive) at the optical port. Typically, the optical port may be covered by a suitable window allowing the x-rays and light to pass out of the housing to the sample and resulting x-ray fluorescence and Raman radiation to pass back from the sample through the window and into the housing, while keeping dust and other contaminants out of the housing. In use, this window may be placed adjacent or against a sample so that the x-rays and light overlap (including being coextensive) on the sample.

In another construction, the analyzer additionally comprises a housing having an optical port and an x-ray port. In this construction the x-ray illuminator illuminates the sample out through the x-ray port and the x-ray spectrometer receives radiation from the sample passing back through the x-ray port. Also, the optical illuminator illuminates the sample out through the optical port and the optical spectrometer receives radiation from the sample passing back through the optical port. A transport moves a sample between a position in which it is illuminated by x-rays from the optical port, and a position in which it is illuminated by light from the optical port. Such a transport may be under control of the processor. This embodiment is not as well suited for a hand-held analyzer, but may be more suited for a portable analyzer. Of course, the transport may not be present and instead an operator could just manually reposition the sample as needed.

Any embodiment of an analyzer of the present invention may be hand-held or portable. By "hand-held" is referenced that the analyzer weighs less than 5 kg, 2, 1, or even less than 0.5 or 0.2 kg, and may have dimensions of less than 50 cm or even 30 cm in each dimension, and one of the dimensions (the thickness) may even be less than 10 cm or 5 or 3 cm. A "hand-held" analyzer will often be battery powered with the battery typically fitting within the foregoing dimensions and included in the foregoing weights, although a separate power supply could be provided and connected to the spectrometer. A "portable" analyzer may be somewhat larger in size, for example less than 50 kg, 20 kg or 10 kg, such as 10 to 50 kg or 20 to 50 kg, and have dimensions somewhat larger (such as up to 500, 200 or up to 100 cm in any one dimension) and typically includes a power input which connects to an external power supply (though a battery may be provided).

As mentioned above, methods of the present invention include any method which can be executed by any apparatus described in this application. Computer program products of the present invention include any computer program product carrying a computer program which can execute any method of the present invention. A computer program "product" is a tangible, non-transitory medium, which may carry a computer program of the present invention (for example, a magnetic, optical, or solid-state memory) in a non-transitory, but potentially temporary, form.

Throughout the present application the following terms have the described meaning unless a usage is clearly to the contrary. Words such as "first" and "second" do not indicate any particular relationship, and are used just to distinguish similarly named elements. It will be appreciated that while different elements of embodiments of the present invention have been described separately, they could in practice use some or all of the same components. For example, the x-ray and Raman spectrometers may use one or more of the same components (such as a same detector) though in practice, they will typically use completely separate components. "Analysis", "analyze", or similar words, reference identifying one or more of an element, molecule, or compound. This identification can be either or both, qualitative (for example, an element is or is not present) or quantitative (for example, the presence of a compound is "high" or likely exceeds a predetermined amount, or is present in a stated amount or concentration). "Identification" references the information presented, and need not be absolutely correct. For example, a processor may determine that an element, molecule, or compound is likely to be present and presents that result as an "identification" with or without additional information that the result is uncertain or has a specified degree of certainty (for example, "molecule X is present with 60% certainty"). A "molecule" is composed of two or more atoms, which may be the same or different, and may carry a charge or not (therefore, a molecule includes cations or anions with multiple atoms). A "compound" is composed of two or more different atoms, so a molecule may be a compound where the atoms of the molecule are different. In analyzing a sample, the analyzed compound may be an analyzed molecule (when made of different elements) or an analyzed molecule which itself is part of a larger compound which optionally includes a further identified element (such as from the x-ray spectral data). For example, sulfate ion is a molecule which may be identified from a Raman signal and iron is an element which may be identified by XRF. If both are found in a sample analysis then, depending upon what else was found by the analysis, an analysis might provide iron sulfate as a likely compound in the sample. A "processor" is any hardware, or hardware and software combination, that can accomplish the tasks required of it. For example, a processor could include a suitably programmed general purpose microprocessor, or an application specific integrated circuit ("ASIC"). In the case where the processor is programmable, it may not yet be programmed but only capable of being loaded with the program required so the processor can then accomplish the tasks required. "Light" reference any electromagnetic radiation in the ultraviolet (100 to 400 nm), visible (400-700 nm), or infra-red (700-2000 nm) ranges. "A" means a single one of a thing and includes more than one. For example, "identifying a first element" means identifying one or more first elements. Similarly, when the processor identifies as a cut-off an elapsed time after the beginning of "a" light pulse, this identification can be accomplished based on data following multiple light pulses (and, for example, an average suitable cut-off may then be identified. Likewise when Raman spectral data is selected from data from the Raman spectrometer produced in response to radiation emitted from the sample within the cut-off after the beginning "a" light pulse, one or more such pulses may be used. "Or" means any one or more of the specified items. For example, "identifies multiple elements or multiple molecule types" includes identifying both multiple elements and multiple molecule types, as well as just only elements or only molecule types. "May" means optionally. For example, if any embodiment of the invention "may have feature X" then that embodiment can actually include feature X or not include feature X. When a range of any quantity is mentioned, that range specifically describes every included whole unit value within that range (for example, "up to 100 picoseconds" specifically describes values which include 1, 2, 3, 4, . . . , 100 picoseconds and the like). All references cited in the present application are fully incorporated herein by reference. However, where anything in an incorporated reference contradicts anything stated in the present application, the present application prevails. The order of any sequence of events in any method recited in the present application, is not limited to the order recited. Instead, the events may occur in any order, including simultaneously, which is logically possible.

Figure 1:
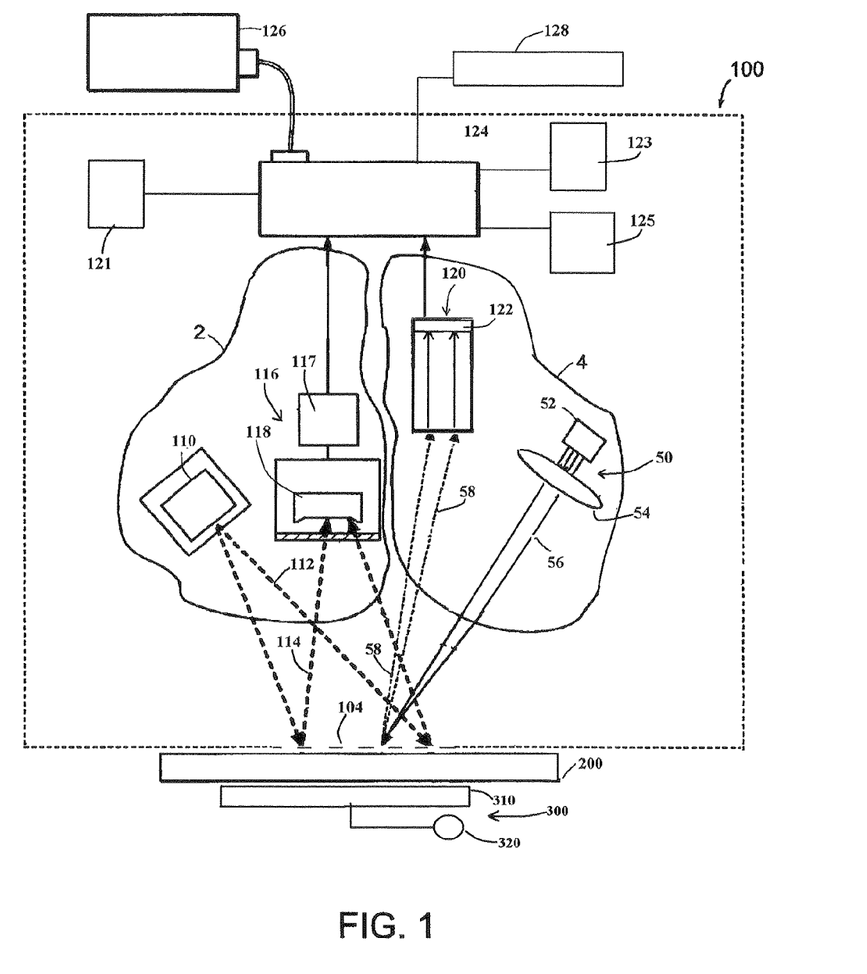
FIG. 1 is a schematic view of an analyzer of the present invention.

Referring now to FIG. 1, the analyzer shown includes a housing 100 typically made of metal or high impact plastic, and which is substantially closed and light-tight except for an optical port defined by a window 104. Window 104 is made of any suitable material transparent to x-rays, UV, and visible light (for example, a suitable polymer film such as polypropylene, polyester (Mylar®), or polyimide (Kapton®)). While some materials for window 104 may also produce a Raman spectrum, the analyzer can store such spectrum in memory and the processor can mathematically eliminate such spectrum from the analysis. An x-ray section 2 within housing 100 includes an x-ray illuminator in the form of an x-ray source 110, and an x-ray spectrometer 116 which includes an x-ray detector 118 and a digital signal processor 124. X-ray source 110 may be a suitable x-ray tube, such as having anode target made of an appropriate metal such as silver, tungsten, molybdenum, rhodium, palladium, tantalum, copper, chromium, gold or titanium. X-ray source 110 is arranged to illuminate a sample 200 with an x-ray beam 112 when the sample is positioned adjacent window 104 and the x-ray source is activated. The x-ray spectrometer 116 is arranged to receive x-ray fluorescence 114 emitted from the sample 200 in response to the illuminating x-ray beam 112, and produce from digital signal processor 124 x-ray fluorescence spectral data representative of the x-ray fluorescence 114. As previously mentioned, in some embodiments the x-ray section 2 may be omitted.

An optical section 4 within housing 100 includes an optical illuminator 50. Optical illuminator 50 includes a light source 52 and various optics 54 (shown schematically as a single lens in FIG. 1) so as to direct a light beam 56 through window 104 to illuminate sample 200 with light. Light source 52 provides a light beam 56 of sufficient intensity for Raman spectroscopy in the UV range. For example, light source 52 may be a UV laser such as a laser of wavelength less than 300 nm, for example 260 nm or less. Note that x-ray beam 112 and light beam 56 overlap at port 154, and could even be coextensive (that is, they both cover the same area on sample 200). In the case of a laser beam, suitable optics could be used to expand it so that it covers the desired area on sample 200. When sample 200 is particularly inhomogeneous, this overlapping increases the chances that x-ray spectral data and Raman spectral data are being collected from a same composition in the sample. Also, the x-ray spectral data will typically represent an average over a surface region (for example, 1 cm$^2$). However, the Raman spectral data could be collected as a scan over the same area as described below, to provide useful data on mineral mapping with the sample, as described below. Optical section 4 further includes a Raman spectrometer 120 which includes detector 122 and various optics (not shown). Raman spectrometer 120 is arranged to receive Raman radiation 58 emitted from a sample 200 in response to illumination by light beam 56, and produce Raman spectral data representative of the Raman radiation so emitted. As illustrated in FIG. 1, the x-ray illuminator 110 is positioned with a path length to optical port 104 which is shorter than the path length from the optical illuminator 50 to optical port 104. That is, the length of x-ray beam 114 to window 104 is shorter than the length of light beam 56 to window 104. Similarly, x-ray spectrometer 116 is positioned with path length from optical port 104 which is shorter than the path length from optical port 104 to Raman spectrometer 120. That is, the path of x-ray fluorescence 114 is shorter than the path of Raman radiation 58.

A processor 124 communicates with x-ray spectrometer 116 and Raman spectrometer 120 to receive x-ray and Raman spectral data (both Stokes and anti-Stokes spectral data) from them, and communicates with x-ray source 110 and optical illuminator 50 to control their operation (for example, controlling their ON and OFF states as described herein). Processor 124 may also control operating parameters of either or both spectrometers 116, 120. Processor further communicates with a memory 121 (such as an optical, magnetic, or solid state memory), a location module 123 which can provide a geographic location of the analyzer (such as a Global Position System chip, or "GPS" chip), and a wireless communication module 125 (such as a cellular, satellite, or Wi-Fi communication module) which allows processor 124 to communicate with remote devices. Programming for processor 124 to execute any of the methods described herein, any pre-selected parameters for any controlling functions, and any other needed data, may be provided by any one or more of memory 121, communication module 125, or an operator interface 128 located on the outside of housing 100. Similarly, memory 121 can store any spectral data produced by either spectrometer or analysis information or data intermediate to an analysis. Operator interface 128 may include navigating buttons which can bring up a virtual keyboard on a display 126 also located to be visible from the outside of housing 100.

Figures 2A, 2B:
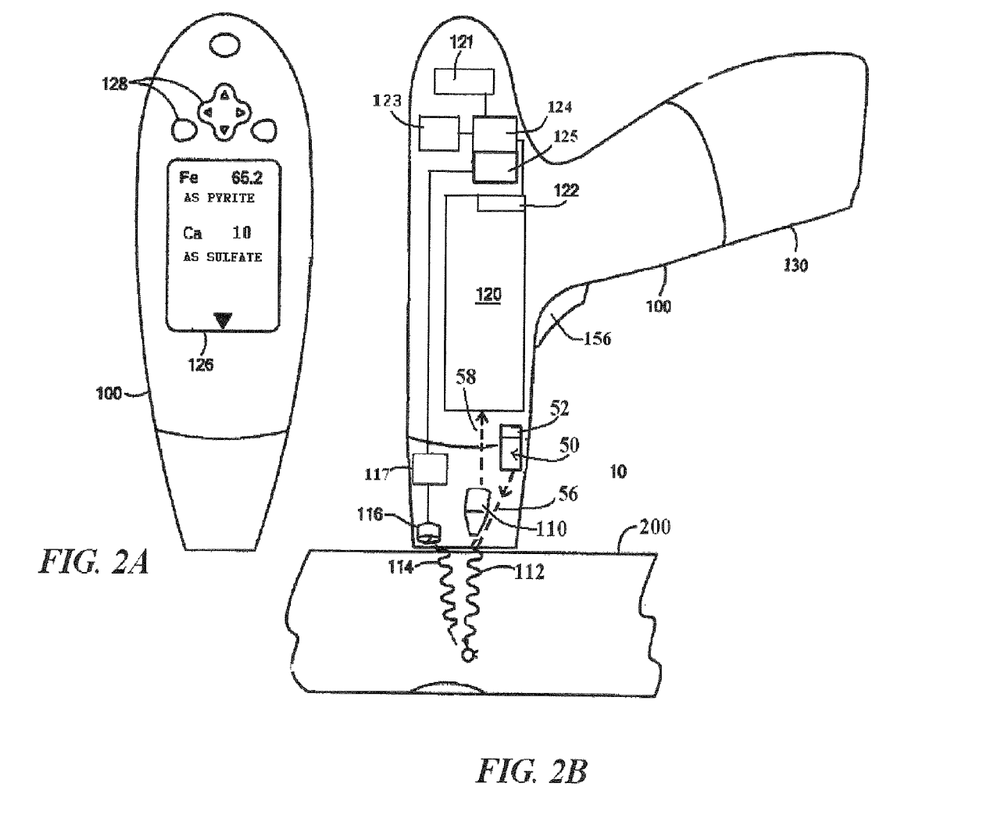
Figure 3:
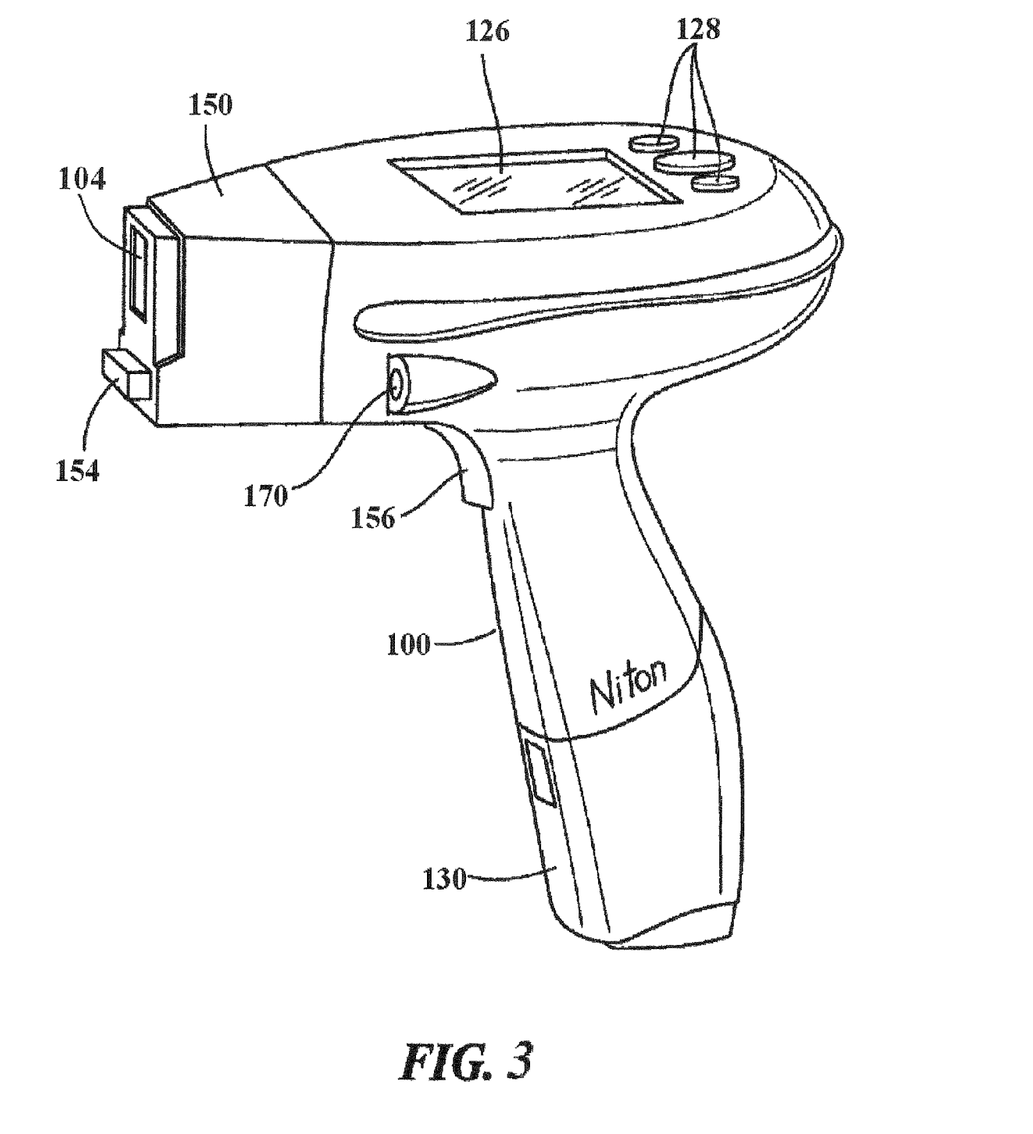
FIG. 3 is a perspective view of a hand-held analyzer of the present invention.

While the analyzer of FIG. 1 may be constructed as a portable analyzer, it may in particular be constructed as a hand-held analyzer such as shown in FIGS. 2 and 3. The hand-held analyzer of FIGS. 2 and 3 has the same components as shown in FIG. 1 with some additional features as now described. In particular, housing 100 is constructed in the shape of a gun for easy holding by a user. The hand-held analyzer also includes a battery 130 (which may be rechargeable) to power all of the analyzer components, a safety interlock switch 154, and a trigger 156. Safety interlock switch 154 is designed to be open and prevent activation of the analyzer until port 154 is immediately adjacent to a sample 200 such that sample 200 will then push switch 154 inward to a closed position. Trigger 156 can be pressed by a user to begin an analysis of a sample when safety interlock switch 154 is closed.

Note that while in the embodiments of FIGS. 1-3 have both the x-ray and optical illumination directed through a same window 104, it is possible to have an analyzer with separate ports for each, as described above. These two separate ports could be adjacent each other, or could be separated by a portion of the housing 100. In such a situation a transport 300 may be provided to move the sample 200 from one window to the next. Transport 200 can include a sample support 310 and motor 320 linked to translate support 310, with motor 320 being controlled by processor 124. In this variation the window for the optical section could then be visible and UV-transparent material such as glass, quartz, silica, sapphire, calcium fluoride, barium fluoride, or the like. Such an embodiment would be particularly useful in portable analyzers which may not be hand-held.

Figure 4A:
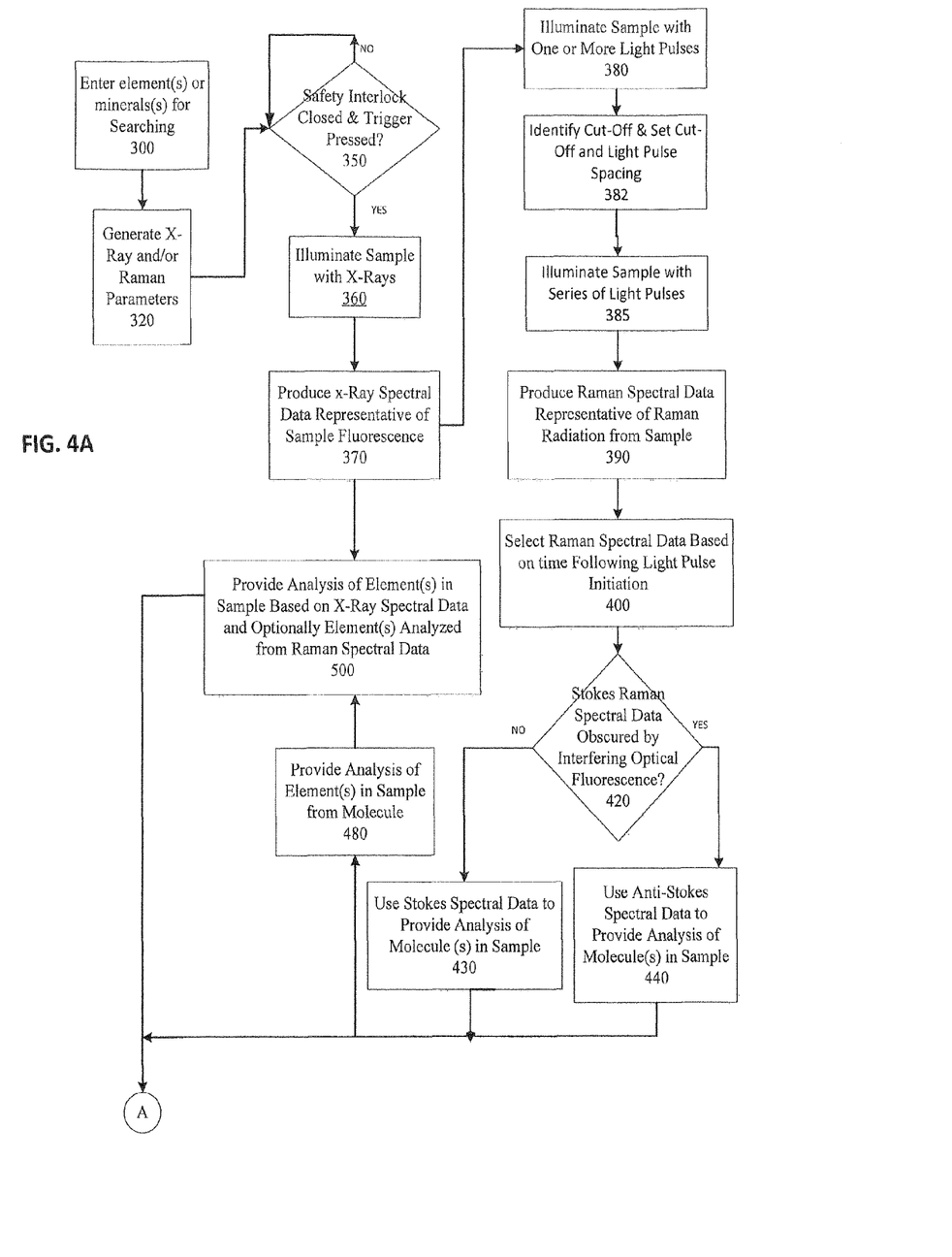
FIGS. 4A and 4B are flowcharts illustrating a method of the present invention.
Figure 4B:
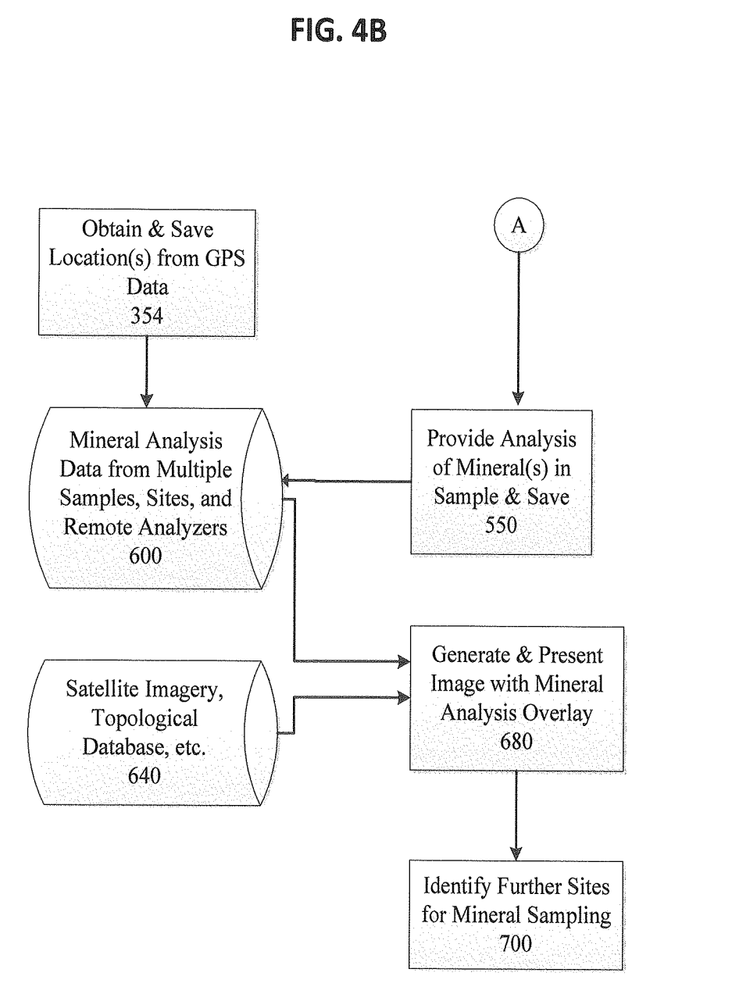

Operation of the hand-held analyzer of FIGS. 2 and 3 will now be described with reference to FIG. 4 although it will be appreciated that such operation is the same as the analyzer shown in FIG. 1 except the safety interlock switch 154 and trigger 156 are present in the hand-held embodiment. It will be assumed that processor 124 has already been suitably programmed to carry out the required tasks, in any of the manners already described. First, a user will grip housing 100 in one hand, then enter (300) information on elements or minerals to be searched using user interface 128 and screen 126. Alternatively, this action can be omitted either because the user wishes to search for all elements or minerals which the analyzer is capable of identifying, or because this information was previously stored in memory 121 (for example, by delivery from communication module 123). Processor 124 then generates (320) any needed preselected parameters for controlling any components of x-ray section 2 or optical section 4, if such parameters were not previously provided from memory 121. Such preselected parameters might include any one or more of: the duration of an x-ray beam 114 delivered from x-ray source 110; light pulse duration, frequency, and total elapsed time for light beam 56 delivered from optical illuminator 50; parameters for evaluating when a Stokes spectra are obscured by interfering optical fluorescence; the time period over which processor 124 will select the Raman spectral data from the Raman spectrometer so as to separate the Raman spectra data from an interfering optical fluorescence signal when present.

Processor 124 then checks (350) if safety interlock switch 154 is closed, which would only normally happen once the user has placed optical port 104 adjacent and against sample 200, and if the user has pressed trigger 156. Once both events are satisfied then processor 124 activates x-ray source 110 to cause it to illuminate the sample 200 with x-ray beam 112 for a preselected period of time. During this time X-ray spectrometer 116 receives any x-ray fluorescence 114 emitted from sample 200 in response to illuminating x-ray beam 112, and produces (370) x-ray spectral data representative of that x-ray fluorescence. Processor 124 then activates optical illuminator 50 (by controlling light source 52) to illuminate (380) sample 200 with one or more light pulses 380. Processor 124 then identifies as a cut-off an elapsed time after the beginning of a light pulse at which optical fluorescence interferes with Raman spectral data, as well as light pulse spacing, and sets (382) these values for a sample or sample type in a manner described above. For example, interfering fluorescence will cause an apparent rise in the signal baseline which eventually may go above any peak values from Raman spectral data. When such a rise has reached a value which has been predetermined to be unacceptable, the time duration from the beginning of the light pulse can be set as the cut-off (or an average or mean used if multiple pulses are used to identify a cut-off). Spacing between light pulses can then also be set (382) as a time which is at least equal to the cut-off time (and preferably somewhat greater than the cut-off time). The same, or a different sample (preferably of the same sample type), can then be illuminated (385) with a series of light pulses using the set light pulse spacing.

During the time each light pulse is ON, Raman spectrometer 120 receives any Raman radiation 58 emitted from sample 200 in response to illuminating pulses of light beam 56 and produces (390) Raman spectral data representative of that Raman radiation (with both Stokes and anti-Stokes components). Processor 124 selects (400) Raman spectral data based on time following the beginning of each light pulse so as to separate Raman spectral data from any interfering optical fluorescence signal if present. In particular, in FIG. 4 processor 124 selects as Raman spectral data that data from the Raman spectrometer produced in response to radiation emitted from the sample within the cut-off after the beginning of one or more light pulses.

Processor 124 also determines (420) if the Stokes spectral data is obscured by interfering optical fluorescence. This determining (420) can be based on a check for one or more clear peaks within typical expected Stokes shifts from the wavelength of illuminating light beam 46 (Stokes shifts being to longer wavelengths than the illuminating light). An intensity check can also be performed since Raman radiation is far weaker than optical fluorescence (so a broad high intensity band in a region of expected Stokes shift would indicate interfering fluorescence). The selecting (400) or determining (420) methods for reducing the effect of interfering optical fluorescence can be used together, as illustrate, or either one can be used without the other. Alternatively, for many samples interfering optical fluorescence will likely be sufficiently low when a short wavelength UV light source 52 is used (for example, about 260 nm or shorter wavelengths) so that both the selecting (400) and determining (420) could be eliminated, and light source 52 need not then provide a series of light pulses.

If processor 124 determines (420) that the Stokes spectral data is obscured by interfering optical fluorescence it uses the anti-Stokes spectral data, and not the Stokes spectral data, to provide (440) an analysis of a molecule in sample 200. On the other hand, if processor 124 determines (420) that the Stokes spectral data is not obscured by an interfering fluorescence then it uses the Stokes spectral data to provide (43) an analysis of a molecule in sample 200. It is typically better to use Stokes spectral data when it is not obscured since Stokes radiation is of higher intensity than anti-Stokes radiation. Of course, if the Stokes spectral data (including any part of that spectral data) is determined (420) not to be obscured then processor 124 could use both the anti-Stokes spectral data, and any Stokes spectral data which is not obscured, in the foregoing molecule analysis.

Steps 380-400 represent an adaptive time gating, method (with steps 380-382 representing the adaptive aspect). However, in some embodiments the adaptive aspect of steps 380-382 could be omitted and step 385 could use a series of light pulses of preselected characteristics as previously described. As previously mentioned, interfering optical fluorescence generally occurs at a later time after the beginning of a light pulse, than does the Raman radiation (which occurs almost instantaneously after the light pulse begins). So processor 124 would identify as Raman spectral data that data from Raman spectrometer 120 which occurs in a first preselected time period following initiation of the light beam, and identify as interfering optical fluorescence that data from Raman spectrometer that occurs after the preselected time period, and select the former as Raman spectral data.

In any event, the analysis of a molecule may be made by comparing the Stokes and/or anti-Stokes spectral data with a database of spectral data in a known manner. Even when there are mixtures of molecules present, known techniques can be used to resolve the different molecule types. The database may either be held in memory 121 or accessed at a remote location using communication module 125. An analysis of one or more elements in sample 200 can then be provided (480) based on the Raman spectral data. This analysis may simply be an identification of the presence of one or more elements, with or without their concentration, based on the analysis of one or more molecules being present in sample 200. This information on an analysis of elements from the Raman spectral data, can then be used together with x-ray spectral data to provide (500) a more accurate quantitative analysis of one or more elements for which an analysis could be provided (500) based on the x-ray spectral data. For example, an initial quantitative analysis on the presence of strontium may have been provided (500) based only on the x-ray spectral data. However, an analysis of the presence of sulfur and oxygen (as sulfate) may have been provided (480) from the Raman spectral data. In this event, processor 124 may then provide (500) a more accurate quantitative analysis of strontium using the sulfur and oxygen analysis and the x-ray spectral data in a fundamental parameter type calculation for strontium.

From the one or more different elements analyzed, and from the molecules analyzed, processor 124 may then provide (550) an analysis of one or more minerals present in sample 200. Again, this can be accomplished by comparing the results with a database of minerals available in memory 121 or accessible at a remote site using wireless communication module 125. For example, if strontium and sulfate have been identified, processor 124 can ascertain from the database that strontium sulfate is a known mineral and therefore likely to be present. Processor 124 can then save (600) the results on the mineral analysis into a database either in memory 121 or a remote location along with the geographical location obtained from location module 123. After multiple samples from different locations have been collected by the analyzer, or by one or more different analyzers which can exchange information either directly or indirectly (such as through a remote database using their communication module 125), multiple locations of different analyzed minerals can be extracted. This can be done by processor 124 accessing memory 121 or accessing a remote memory using communication module 125, or can be done by a remote processor and communicated to processor 124 using communication module 125. In any event, processor 124 can then generate and present (680) a satellite, topological, or map image or other geographical information obtained (640) from a suitable database, overlaid with the extracted mineral analysis information on display 126. Using the foregoing information, processor 124 or a remote processor, may identify (700) further sites for mineral sampling and present those site locations or other instructions to for collecting further mineral samples, on display 126. For example, a preselected grid of an area to be explored may have obvious missing locations which processor 124 can identify for further sample analysis.

As mentioned above, the x-ray spectrum is typically collected from larger area, for example 1 square centimeter, and therefore represents an average over that area while the Raman signal comes from a much smaller are, typically about 1 square millimeter. Therefore, in a variation of the embodiment described, optical illuminator 50 can be constructed with suitable optics to allow light beam 56 to be scanned across sample 200 under control of processor 124 (such as by a raster scan). In operation the illumination (380) with light will then be by scanning the light beam 56 (including scanning pulses of beam 56, when used) across an area on the sample (for example, in a raster scan). That is, the Raman spectrometer is run in a scanning mode, with a laser beam of 1 square millimeter scanned across the area from which the x-ray spectrum is collected (for example, about 1 square centimeter). This feature allows mineral mapping across an area on sample 200 within the field of view of the x-ray spectrometer. A Raman scan of such an area could be easily accomplished during a typical x-ray exposure time of 30 sec.

Further Examples

In one example, if the elements Fe and S are both identified from the x-ray spectral data, the sample could be Iron Sulfide (FeS), Magnetite ($Fe_3O_4$) with free S, Pyrite ($FeS_2$), or Pyrrhotite ($Fe_7S_8$). The Raman spectral data can be used to identify the molecule types present and hence the compounds of the mineral composition, in the manner previously described. Once the mineral composition is analyzed, for example that the sample is evaluated to be FeS, $FeS_2$ or $Fe_3O_4$, the analyzer can properly account in XRF calculations for the presences of oxygen in the sample (which is not seen by the XRF), and obtain a more accurate quantitative result for iron and sulfur. Similarly, if XRF spectral data analysis identifies the presence of calcium, sulfur and iron, an analysis of Raman spectra data may determine whether sample contains calcium sulfate or calcium carbonate or both (carbon being another element not analyzed directly by XRF).

Figure 5A:
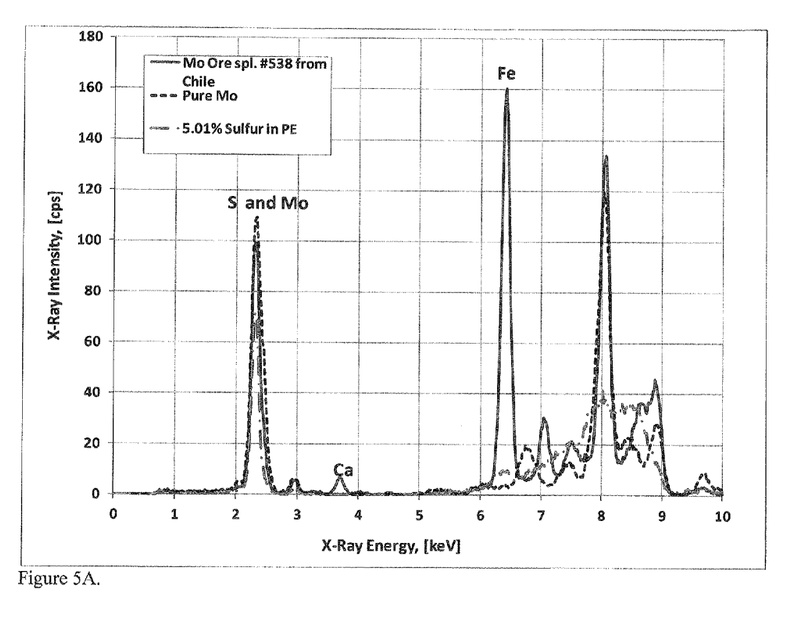
FIGS. 5A and 5B illustrate another example of applying the present invention to mineral analysis.
Figure 5B:
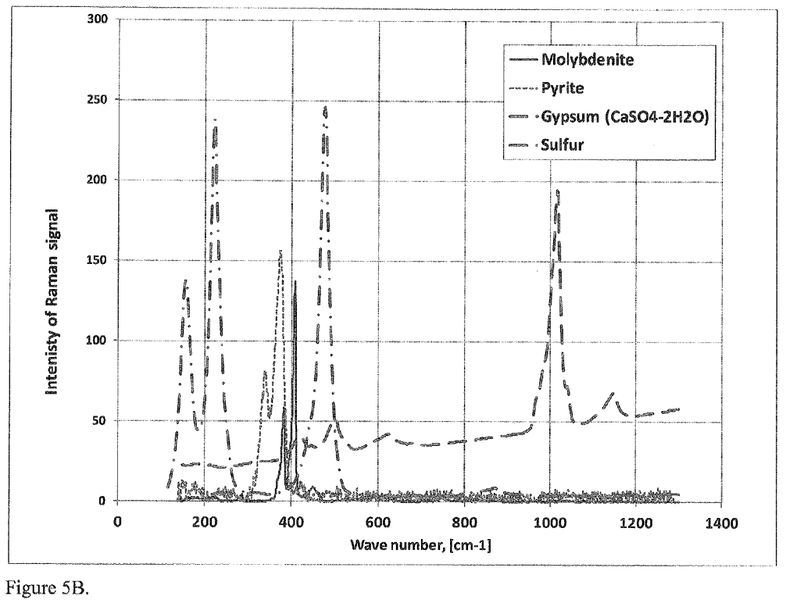

Another example is analysis of molybdenum rock or ore. Molybdenum metal is recovered from its most abundant ore, mineral molybdenite, which is molybdenum disulfide, $MoS_2$. However, in such ore there are usually other compounds which may also contain sulfur such as pyrite ($FeS_2$) or calcium sulfate. X-ray analysis of such material is complicated by the fact that molybdenum atoms when excited produce not only their main characteristic x-rays at 17.4 keV but also characteristic x-rays at energy identical to that of the sulfur x-rays, that is at 2.3 keV. Presence of x-ray signals from iron and calcium also implies possibility of sulfur presence. Therefore, the intensity of x-rays measured by the XRF section of the instrument at 2.3 keV energy is a potential composite of sulfur x-rays from pyrite, calcium sulfate, molybdenum disulfide and of 2.3 keV x-rays from molybdenum itself. Using Raman spectral data it is possible to identify which of the compounds containing sulfur is present in the sample. Specifically, it is possible to determine whether the sample contains molybdenum disulfide or molybdenum oxide (both compounds would produce x-rays at 2.3 keV, one from sulfur and molybdenum the other from just molybdenum). Such information when fed to XRF analytical software would allow for much more accurate elemental analysis of the sample. This example is illustrated by low energy range x-ray spectra of molybdenite pure, molybdenum and pure sulfur, shown FIG. 5A and the Raman spectra of 5B. FIG. 5A shows the low energy range X-ray spectra of Mo ore, pure Mo and pure S. The Mo ore spectrum shows the presence of Calcium and Iron so that peak at 2.3 keV may represent composite of sulfur K-a and Mo-La lines, both at 2.3 keV. FIG. 5B shows the Raman spectra of minerals molybdenite, gypsum (calcium sulphite), pyrite and sulfur. As is seen all minerals produce Raman spectra with different peak features (non-overlaping, at different wave numbers) that clearly distinguish them. Based on such information the X-ray intensity at 2.3 keV may be properly apportioned between sulfur Ka and Molybdenum La lines and thus improve overall accuracy of elemental analysis of the sample.

Particular embodiments of the present invention have been described in detail above. However, it will be apparent that variations and modifications of the described embodiments are possible. For example, it will be appreciated that operations in the methods described can be performed in the order described or in any other order, or simultaneously, that is logically possible. In one such variation steps 500, 520 in FIG. 14 could be performed, for example, before step 400 or at some other time before step 530. Accordingly, the present invention is not limited by the embodiments described.

We claim:

1. An analyzer for analyzing a composition of a sample, comprising:
   an x-ray illuminator to illuminate the sample with x-rays;
   an x-ray spectrometer to produce x-ray spectral data representative of fluorescence radiation emitted from the sample in response to the illuminating x-rays;
   an optical illuminator to illuminate the sample with light;
   a Raman spectrometer to produce Raman spectral data that includes Stokes spectral data and anti-Stokes spectral data representative of Raman radiation emitted from the sample in response to the light; and
   a processor to receive the x-ray spectral data and Raman spectral data and to determine if the Stokes spectral data is obscured by an interfering optical fluorescence signal and, when the Stokes spectral data is determined to be obscured, to use the anti-Stokes spectral data and not the Stokes spectral data, to identify the molecule and provide an analysis of a compound in the sample based on both.

2. An analyzer according to claim 1 wherein the processor:
   identifies a first element of the compound based on the x-ray spectral data;
   identifies a molecule of the compound based on the Raman spectral data; and
   identifies the compound based on the identified element and identified molecule.

3. An analyzer according to claim 2 wherein the processor identifies multiple elements or multiple molecule types.

4. An analyzer according to claim 1 wherein the processor controls the x-ray and optical illuminators so as to turn them on sequentially or simultaneously.

5. An analyzer according to claim 1 wherein the processor:
   identifies a first element of the compound based on the x-ray spectral data;
   identifies a presence of a second element based on the Raman spectral data; and
   provides a quantitative analysis of the first element based on the x-ray spectral data and the identified presence of the second element.

6. An analyzer according to claim 1 wherein the optical illuminator illuminates the sample with light of a wavelength shorter than 300 nm.

7. An analyzer according to claim 1 wherein the processor uses the Stokes spectral data and not the anti-Stokes spectral data when the Stokes spectral data is determined not to be obscured.

8. An analyzer according to claim 1, additionally comprising a housing having an optical port, and wherein:
   the x-ray illuminator, the optical illuminator, and the spectrometers are positioned within the housing such that the x-ray illuminator and optical illuminator illuminate the sample out through the optical port and the spectrometers receive radiation from the sample passing back through the optical port;
   the x-ray illuminator is positioned with a shorter path length to the optical port than the optical illuminator; and
   the x-ray spectrometer is positioned with a shorter path length from the optical port than the Raman spectrometer.

9. An analyzer according to claim 8 wherein the analyzer is a hand-held analyzer.

10. An analyzer according to claim 1 additionally comprising a housing having an optical port, and wherein:
    the x-ray illuminator, the spectrometers, and the optical illuminator are positioned within the housing such that the x-ray and optical illuminators illuminate the sample out through the optical port and the spectrometers receive radiation from the sample passing back through the optical port; and
    the x-ray and optical illumination overlap at the optical port.

11. An analyzer according to claim 1 wherein the x-ray and optical illumination are coextensive at the sample.

12. An analyzer according to claim 1 wherein:
    the optical illuminator illuminates the sample with a light pulse; and
    the processor selects the Raman spectral data from the Raman spectrometer on the basis of time following a beginning of the light pulse so as to separate the Raman spectra data from an interfering optical fluorescence signal when present.

13. An analyzer according to claim 12 wherein the processor selects the Raman spectral produced in response to radiation emitted from the sample within 1 microsecond after the beginning of the light pulse.

14. An analyzer according to claim 12 wherein the processor controls the optical illuminator to produce a series of light pulses which are spaced by at least 1 microsecond.

15. An analyzer according to claim 1 wherein:
    the optical illuminator illuminates the sample with a light pulse; and
    the processor identifies as a cut-off an elapsed time after the beginning of a light pulse at which optical fluorescence interferes with Raman spectral data, then selects as Raman spectral data that data from the Raman spectrometer produced in response to radiation emitted from the sample within the cut-off after the beginning a light pulse.

16. An analyzer according to claim 15 wherein the processor controls the optical illuminator to produce a series of light pulses which are spaced by at least the cut-off time.

17. An analyzer according to claim 1 wherein the optical illuminator comprises a scanning optical illuminator which illuminates the sample with a beam of light scanned across an area on the sample.

18. An analyzer according to claim 1 additionally comprising a housing having an optical port and an x-ray port, and wherein:
the x-ray illuminator illuminates the sample out through the x-ray port and the x-ray spectrometer receives radiation from the sample passing back through the x-ray port;
the optical illuminator illuminates the sample out through the optical port and the optical spectrometer receives radiation from the sample passing back through the optical port;
a transport which moves the sample between a position in which it is illuminated by x-rays from the optical port, and a position in which it is illuminated by light from the optical port.

19. An analyzer for analyzing a composition of a sample, comprising:
an optical illuminator to illuminate the sample with light;
a Raman spectrometer to produce Raman spectral data representative of Raman radiation emitted from the sample in response to the light, wherein the Raman spectral data includes both Stokes spectral data and anti-Stokes spectral data; and
a processor to identify a molecule in the sample based on the Raman spectral data;
wherein:
the processor determines if the Stokes spectral data is obscured by an interfering optical fluorescence signal; and
when the Stokes spectral data is determined to be obscured uses the anti-Stokes spectral data and not the Stokes spectral data to identify the molecule.

20. A method of analyzing a mineral sample, comprising:
illuminating the sample with x-rays;
producing x-ray spectral data representative of fluorescence radiation emitted from the sample in response to the x-rays;
illuminating the sample with light;
producing Raman spectral data that includes Stokes spectral data and anti-Stokes spectral data in response to Raman radiation emitted from the sample in response to the light;
determining if the Stokes spectral data is obscured by an interfering optical fluorescence signal, and when the Stokes spectral data is determined to be obscured, using the anti-Stokes spectral data and not the Stokes spectral data to identify a molecule of the compound; and
providing an analysis of a compound in the sample based on the x-ray spectral data and the Raman spectral data.

21. A method according to claim 20 wherein the providing the analysis comprises:
identifying a first element of the compound based on the x-ray spectral data;
identifying a second element based on the Raman spectral data; and
providing a quantitative analysis of the first element based on the fluorescence spectral data and a presence of the second element.

22. A method according to claim 20 wherein the illuminating the sample with light comprises scanning a beam of light across an area on the sample.

23. A method of analyzing a mineral sample, comprising:
illuminating the sample with light;
producing Raman spectral data representative of Raman radiation emitted from the sample in response to the light, wherein the Raman spectral data comprises Stokes spectral data and anti-Stokes spectral data;
identifying a molecule in the sample based on the Raman spectral data;
wherein the method additionally comprises:
determining if the Stokes spectral data is obscured by an interfering optical fluorescence signal; and
when the Stokes signal is determined to be obscured, identifying the molecule based on the anti-Stokes spectral data and not the Stokes spectral data.

24. A computer program product carrying a computer program which, when loaded into a programmable processor, executes the method of:
controlling an x-ray illuminator to illuminate a sample with x-rays;
receiving x-ray spectral data representative of x-ray fluorescence emitted from the sample in response to the x-rays;
controlling an optical illuminator to illuminate the sample with light;
receiving Raman spectral data that includes Stokes spectral data and anti-Stokes spectral data representative of Raman radiation emitted from the sample in response to the light;
determining if the Stokes spectral data is obscured by an interfering optical fluorescence signal, and when the Stokes spectral data is determined to be obscured, using the anti-Stokes spectral data and not the Stokes spectral data; and
providing an analysis of a compound in the sample based on both the x-ray fluorescence spectral data and the Raman spectral data.

* * * * *